(12) United States Patent
Hogan

(10) Patent No.: US 8,605,290 B2
(45) Date of Patent: Dec. 10, 2013

(54) PRECISION MEASURING SYSTEM

(76) Inventor: Josh N Hogan, Los Altos, CA (US)

( * ) Notice: Subject to any disclaimer, the term of this patent is extended or adjusted under 35 U.S.C. 154(b) by 773 days.

(21) Appl. No.: 12/800,836

(22) Filed: May 23, 2010

(65) Prior Publication Data

US 2010/0241007 A1      Sep. 23, 2010

Related U.S. Application Data

(63) Continuation-in-part of application No. 11/048,694, filed on Jan. 31, 2005, now Pat. No. 7,751,862.

(51) Int. Cl.
*G01B 11/02* (2006.01)

(52) U.S. Cl.
USPC .............................. 356/497; 356/479; 356/489

(58) Field of Classification Search
USPC ................................................. 356/479, 497
See application file for complete search history.

(56) References Cited

U.S. PATENT DOCUMENTS 6,198,540 B1 * 3/2001 Ueda et al. .................... 356/479
6,728,571 B1 * 4/2004 Barbato ........................ 600/478

* cited by examiner

*Primary Examiner* — Tarifur Chowdhury
*Assistant Examiner* — Jonathon Cook

(57) ABSTRACT

A non-invasive imaging and analysis method and system/apparatus suitable for non-invasive imaging and analysis of a target is disclosed. Targets include biological tissue structures or components; optical structures or components; electronic structures or components; or structures in general. A preferred embodiment of the invention provides a precision optical measuring module that modifies the spatial separation of multiple reference interference signals by adjusting the separation between a partial reflective element and a full mirror mounted on a piezo device and determining the distance between surfaces or structures within the target by simultaneously monitoring the magnitude of the separation between the partial reflective element and the full mirror and processing generated interference signals. Techniques for simultaneously monitoring the magnitude of the separation between the partial reflective element and the full mirror include conventional measurement techniques, such as, capacitive, optical, or strain techniques or alternatively the use of one or more etalons. Another embodiment of the invention provides a system and method of precisely measuring the position of a surface of interest.

13 Claims, 5 Drawing Sheets

PRECISION MEASURING SYSTEM

CROSS REFERENCES TO RELATED APPLICATIONS

This application, 12/800,836, is a continuation in part of U.S. utility application with Ser. No. 11/048,694, filed on Jan. 31, 2005 now U.S. Pat. No. 7,751,862 titled "Frequency Resolved Imaging System", the contents of which are incorporated by reference as if fully set forth herein. This application also relates to U.S. utility application Ser. No. 11/025,698 filed on Dec. 29, 2004 titled "Multiple reference non-invasive analysis system", the contents of which are incorporated by reference as if fully set forth herein. This application also relates to U.S. utility application Ser. No. 10/949,917 filed on Sep. 25, 2004 titled "Compact non-invasive analysis system", the contents of which are incorporated by reference as if fully set forth herein.

FIELD OF THE INVENTION

The invention relates to non-invasive optical imaging and analysis of targets. Targets include biological tissue structures or components; optical structures or components; electronic structures or components; or structures in general. The invention includes a precision optical measuring module suitable for precision measurement of the relative location of surfaces or structure interfaces.

BACKGROUND OF THE INVENTION

Non-invasive imaging and analysis is a valuable technique for acquiring information about systems or targets without undesirable side effects, such as damaging the target or system being analyzed. In the case of analyzing living entities, such as human tissue, undesirable side effects of invasive analysis include the risk of infection along with pain and discomfort associated with the invasive process.

In the particular case of non-invasive in-vivo imaging and analysis of biological tissue structures or components, such as structures or components of the eye, it is desirable to measure the physical size of structures or components of the eye under various conditions, for example to monitor for the onset of glaucoma or for other ophthalmic related purposes. A non-invasive method with increased precision enables more accurate monitoring of conditions of the eye.

Various versions of optical coherence tomography (OCT), are currently used to image and analyze targets, such as the human eye, non-invasively. One version of OCT uses a superluminescent diode (SLD) as the optical source, The SLD output beam has a broad bandwidth and short coherence length.

The technique involves splitting the output beam into a probe and reference beam. The probe beam is typically applied to the target to be analyzed. Light scattered back from the target is combined with the reference beam to form the measurement signal. Because of the short coherence length only light that is scattered from a depth within the target such that the total optical path lengths of the probe and reference are equal combine interferometrically.

Thus the interferometric signal provides a measurement of the scattering value at a particular depth within the target. By varying the length of the reference path length, a measurement of the scattering values at various depths can be measured and thus the scattering value as a function of depth can be measured, providing image or analytic information.

In conventional OCT systems depth scanning is achieved by modifying the relative optical path length of the reference path and the probe path. The relative path length is modified by such techniques as electro-mechanical based technologies, such as galvanometers or moving coil actuators, rapid scanning optical delay lines and rotating polygons. All of these techniques involve moving parts that have to move a substantial distance, which have limited scan speeds and present significant alignment and associated signal to noise ratio related problems.

Motion occurring within the duration of a scan can cause significant problems in correct signal detection. If motion occurs within a scan duration, motion related artifacts may be indistinguishable from real signal information in the detected signal, leading to an inaccurate measurement. Long physical scans, for larger signal differentiation or locating reference areas, increase the severity of motion artifacts. Problematic motion can also include variation of the orientation of a target surface (such as skin) where small variations can have significant effects on measured scattering intensities.

Non-moving part solutions, include acousto-optic scanning, can be high speed, however such solutions are costly, bulky and have significant thermal control and associated thermal signal to noise ratio related problems. Optical fiber based OCT systems also use piezo electric fiber stretchers. These, however, have polarization rotation related signal to noise ratio problems and also are physically bulky, are expensive, require relatively high voltage control systems and also have the motion related issues.

These aspects cause conventional OCT systems to have significant undesirable signal to noise characteristics and present problems in practical implementations with sufficient accuracy, compactness and robustness for commercially viable and accurate imaging and analysis devices. Therefore there is an unmet need for commercially viable, compact, robust, non-invasive imaging and analysis technology and device with sufficient accuracy, precision and repeatability to image or analyze targets and in particular to image and analyze biological structures.

SUMMARY OF THE INVENTION

The invention described herein meets at least all of the aforementioned unmet needs. The invention provides a method and system for a non-invasive imaging and analysis of targets. Targets include biological tissue structures or components; optical structures or components; electronic structures or components; or structures in general.

The invention includes a radiation source and a radiation signal processing system which provides a probe and a composite reference beam. It also includes a means for applying the probe beam to the target to be analyzed, recombines the scattered probe beam and the composite reference beam interferometrically and simultaneously acquires information from different locations within the target.

The invention includes a method of modifying the depth or spatial separation of the different locations within the target from which information is acquired simultaneously and also includes a precision optical measuring module suitable for precision measurement of the relative location of surfaces or structure interfaces. It further includes electronic control and processing systems.

DETAILED DESCRIPTION OF THE INVENTION

Figure 1:
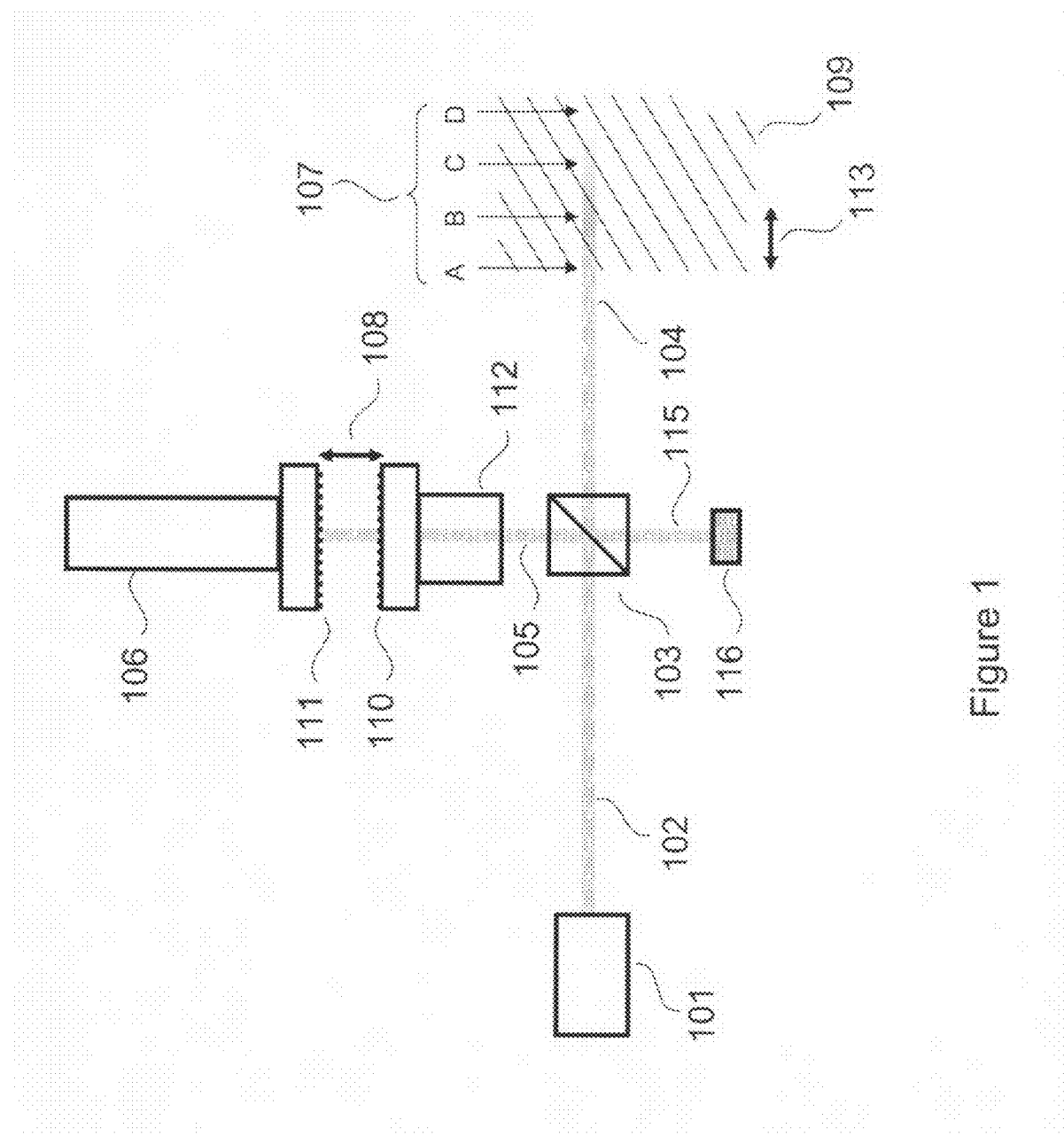
FIG. 1 is an illustration of a non-invasive imaging and analysis system according to the invention.

Conventional optical coherence tomography is based on splitting the output of a broadband optical source into a probe beam and a reference beam and of varying the optical path length of the reference beam to scan the target. This approach has problems and limitations including problems and limitations related to motion occurring within the duration of a scan.

A novel interferometric approach which addresses these problems and limitations by simultaneously acquiring multiple meaningful interferometric signals from multiple depths within the target, thus avoiding relative motion artifacts, is described in application Ser. Nos. 11/025,698 and 11/048,694 (of which this application is a continuation in part) and both of which are incorporated by reference as if fully set forth herein. With the present invention the scanning capability and precision is increased.

As with inventions described in the applications incorporated by reference, the present invention involves generating composite reference radiation (also referred to as a composite reference beam) consisting of multiple component radiation (also referred to as component reference beams) each having a different path length. In addition to having different path lengths, the components of the composite reference radiation are also effectively modulated at different frequencies by imposing different frequency content on the different components of the composite reference radiation.

Imposing different frequency content on the different components of the composite reference radiation enables forming a composite interferometric signal by combining the composite reference radiation with a portion of probe radiation scattered by a target of interest. The composite interferometric signal can be processed to provide information corresponding to different components of the composite reference. Accordingly the inventive system can simultaneously acquire and analyze information from different depths within a target while scanning the target in a manner that avoids undesirable motion related artifacts.

As used herein radiation means optical radiation and is also referred to as a beam, the reference radiation is referred to as a reference beam and the probe radiation as a probe beam. The component reference beams are generated by a combination of a partially reflective element and a highly reflective element. The separation of these two reflective elements is varied to change the path length of the component reference beams. The multiple component reference beams are generated by multiple reflections between these two reflective elements.

The range of scan of different component reference beams increases with the multiplicity of reflections (also referred to as the multi pass order, N) enabling a significantly larger scan range at deeper levels within the target. Deeper scans may also overlap allowing improved performance.

The deeper larger scans occur at the same repetition rate as the smaller scans and therefore have no increased sensitivity to motion. A smaller first order scan enables higher speed scanning while still generating larger scan ranges at deeper (multiple reflection) levels.

In addition to having different magnitude scan ranges, the scans due to different multiple reflections generate interferometric signal with different frequency content enabling the interferometric information from the different component reference beams corresponding to different depth scans to be separated by electronic processing. This enables a compact processing system which can simultaneously acquire and analyze information from different depths within a target and thereby avoid undesirable motion related artifacts.

A preferred embodiment of this invention is illustrated in and described with reference to FIG. 1, which depicts a non-invasive optical analysis system. The analysis system includes an optical processing system that generates a probe beam and a reference beam from a broadband optical source 101 such as a super-luminescent diode (SLD) or a mode-locked laser, whose collimated output beam 102 consists of a broad band, continuous or discrete set of wavelengths.

The output beam 102, is passed through a beam splitter 103, to form a probe beam 104 and a reference beam 105 (which also becomes the composite reference beam on its return path). The probe beam 104 is applied to the target 109 of interest. At least part of the radiation of the beam applied to the target is scattered back and captured form captured scattered probe radiation.

Scattering occurs because of discontinuities, such as changes of refractive index or changes in reflective properties, in the target. If the probe radiation is applied to flat surfaces, such as those of an etalon, reflection will occur, which for purposes of this disclosure may be regarded as a special case of scattering. The captured scattered (or reflected) probe radiation returns back to the beam splitter 103.

In the preferred embodiment, the reference beam 105 is partially reflected by the partial reflective element 110. A portion of the reference beam is also transmitted through the partial reflective element 110 which is then reflected by the modulating reflective element 111 to form a once modulated reference beam.

Modulation can be achieved by having the modulating reflective element 111 mounted on a length modifying device 106 such as a piezo device. A portion of the once modulated reference beam is transmitted through the partial reflective element 110 to form a component of the composite reference beam 105. The modulation imposes a first frequency content on this component of the composite reference beam.

A portion of the once modulated reference beam is also reflected by the partial reflective element 110 and is again reflected and further modulated by the modulating reflective element 111. A portion of this twice modulated reference beam is then transmitted through the partial reflective element 110 to form another component of the composite reference beam 105 with higher frequency content, than the first frequency content, imposed on this second component reference beam and a portion also is reflected by the partial reflective element 110 to form further components of the composite reference beam that are multiple times modulated reference beams each with higher imposed frequency content.

In this manner a composite reference beam 105 is generated that has multiple interferometrically significant components that correspond to depth locations within the target 109. A subset of depth locations 107 are indicated by the set of arrows labeled A, B, C and D. The depth location indicated by the arrow labeled "A" corresponds to the modulating reflective element 111 and would have a corresponding interference signal with a frequency content determined by the motion (repetition rate and magnitude) of the modulating reflective element 111 (single pass or order "1" pass or first order).

Depth location "B" corresponds to a double pass (or order "2" multiple pass) between the modulating reflective element 111 and the partially reflective element 110 and would have a corresponding interference signal with a frequency content twice that of the interference signal corresponding to depth location "A". The depth difference or separation 113 of "B" with respect to "A" within the target 109 is determined by the spatial separation 108 between the partial reflective element 110 and the modulating reflective element 111 modified by the refractive index of the target 109.

Depth location "C" corresponds to a triple pass (third order or order 3 pass) between the modulating reflective element 111 and the partially reflective element 110 and would have a corresponding interference signal with a frequency content three times that of the interference signal corresponding to depth location "A".

Depth location "D" corresponds to a quadruple pass (forth order or order 4 pass) between the modulating reflective element 111 and the partially reflective element 110 and would have a corresponding interference signal with a frequency content four times that of the interference signal corresponding to depth location "A". Interference signals corresponding to higher order multiple passes with correspondingly higher frequencies could also exist. In general, the resulting composite interference signal will have multiple interference components which contain information simultaneously obtained from multiple depth locations.

There is a decrease in the intensity of the reference beam components corresponding to higher order multiple passes. The amount of this decrease in intensity depends on the partially reflecting element. For example, if the partial reflective element reflects 80% and transmits 20% of the reference beam, then the reference beam component from the partially reflective element 110 will have a relative intensity of approximately 80%; the reference beam component from a single pass to the modulating reflective element 111 (corresponding to A) will have a relative intensity of approximately 4%. Partial reflection other than 80% can be used. These relative intensities are approximate because of absorption, scattering, physical imperfections and other noise effects.

Similarly, the reference beam component from a double pass to the modulating reflective element 111 (corresponding to B) will have a relative intensity of ~3.2% and higher order reference signals will have a gradually reducing relative intensity.

The modulating reflective element 111 affects the different component reference beams by different magnitudes corresponding to different path lengths due to reflecting a different number of times. This causes different component reference beams to be modulated by different magnitudes. This, in turn, causes the resulting interferometric signals corresponding to different component reference beams and thereby to different depths (within the target) to have different frequency components which allows the interferometric information from the different depths to be separated by electronic filtering.

The frequencies of the different interference signals are all determined by the single pass piezo scan multiplied by the number of reflections (or the order of the multiple pass, N). This relationship also means the different frequencies are all harmonically related which facilitates separating them by digital signal processing or analog filtering.

At least a part of the modulated reflected component reference beams are re-combined after they pass through the partially reflective element 110 towards the beam-splitter 103 to form a re-combined reference beam which returns along the path of the reference beam 105 and is referred to herein as a composite reference beam. The reflected re-combined reference beam, or composite reference beam, is combined with the captured scattered probe radiation in the beam splitter 103.

The optical element typically referred to as a beam splitter 103 also operates as an optical combining element, in that it is in this element that reflected re-combined reference beam and captured scattered probe radiation are combined. The resulting composite interference signal 115 is detected by the optoelectronic detector 116 to form a composite electronic signal.

A meaningful interferometric signal only occurs with interaction between the reference beam and light scattered from a distance within the target such that the total optical path lengths of both reference and probe paths are equal or equal within the coherence length of the optical beam. In this preferred embodiment simultaneous information from multiple different depth locations is simultaneously acquired and analyzed.

The preferred embodiment also includes an electronic processing module which interacts with an electronic control module (not depicted) by means of electronic signals. The control module provides timing signals, to provide the electronic processing module (also not depicted) with timing signals to assist the processing module with filtering and processing the detected composite interferometric signals. The control module also generates control and drive signals for the system, including signals which modulates the modulating reflective element 111.

In the preferred embodiment, the modulating reflective element 111 is mounted on a length modifying device 106, such as piezo-electric device, which enables performing scans within the target. The different multiple pass component reference beams have increasingly larger magnitude scans.

For example, if the translation range of the modulating reflective element 111 is 20 microns, the range within the target corresponding to the interferometric signal of the single pass, i.e. at location "A", would be 20 microns. This could be regarded as a 20 micron scan. However if the depth resolution of the SLD is of the order of 20 microns there is little meaningful scanning capability.

The range within the target corresponding to the interferometric signal of the tenth multiple pass however would be 200 microns and would represent a significant scanning range. This amplification of scanning range by multiple passes of the reference beam provides an effective method of generating a significant scanning range, without large magnitude translations of the modulating reflective element 111.

Figure 2:
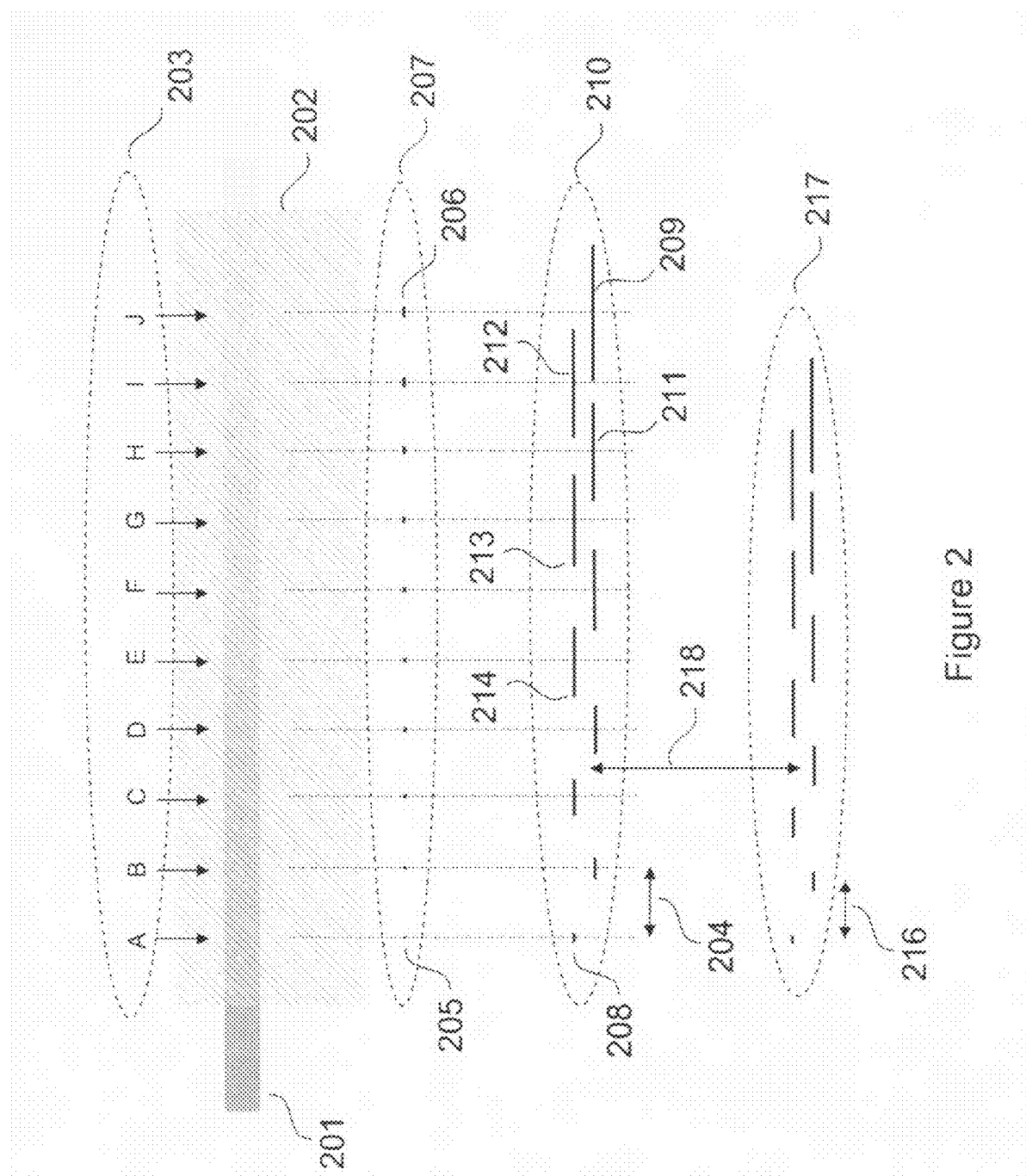
FIG. 2 illustrates examples of non-overlapping and overlapping segments of a Scan according to the invention.

This amplification of scanning magnitude is illustrated in FIG. 2. FIG. 2 illustrates overlapping and non-overlapping segments of scans provided by the inventive system. The probe beam 201 is applied to the target 202. A set of target regions 203 is indicated by the set of arrows labeled A, B, C, D, F, F, G, H, I, J. These arrows indicate depth locations of the center points of scans within the target 202 separated by a distance determined by the separation between the partially reflective element 110 and the modulating reflective element 111 (of FIG. 1) modified by refractive indices and indicated by the depth separation 204.

A set of scans 207 are denominated by the marks "A" through "J". The different lengths of the marks comprising 207 represent the different ranges scanned around the depth locations. For example 205 represents a small range while 206 represents a scan range of ten times the range of 205. The separation between the partially reflective element 110 and the modulating reflective element 111 (of FIG. 1) can be set to provide a depth separation 204 of, for example, 100 microns. If the single pass piezo scanning range is 2 microns (at depth location "A" for example), the scanning range of the tenth pass (or tenth of the multiple reflection set) will be 20 microns (at depth location "J").

The complete set of gradually increasing scan ranges, indicated by the set of marks 207, extend over a region of the target in excess of 1 mm. If, as another example, The separation between the partially reflective element 110 and the modulating reflective element 111 (of FIG. 1) is set to provide a depth separation 204 of 500 microns, the set of marks representing scan ranges would extend over a region of the target in excess of 5 mm. As used herein, the word Scan means a set of scans with gradually increasing scan ranges at multiple depths in the target. The portion of Scan at any depth location is referred to as a segment.

Referring again to FIG. 2 a second Scan 210 is comprised of scan segments, where the single pass piezo scanning range is greater, for example, 20 microns, indicated by the line 208, the scanning range of the tenth pass (or tenth of the multiple reflection set) will be 200 microns, indicated by the line 209, which is a substantial scanning range. The complete set of gradually increasing scan ranges are indicated by the set of marks, expanding from the line 208 to the line 209, enclosed by the dashed oval 210. The vertical offset of alternate lines within the set is for clarity purposes only and has no other significance. All of these lines indicate locations in the target intersected by the horizontal probe signal 201.

The higher order scans overlap adjacent scans, providing a method for achieving a complete scan of a region. For example the scan 211 corresponding to the region indicated by the arrow labeled "H" of the set 203 clearly overlaps the two adjacent scans 212 and 213. In the example of scans enclosed in the oval 210 completely scan the region of the target from the front (left end or less deep portion) of scan 214 to as deep as a detectable scattered signal emerges from the target and for which a significant component reference signal is available.

Thus the region defined by the scan 214 to at least scan 219 can be completely scanned making this technique suitable for imaging as well as analysis. Some portions of deeper regions are scanned by at least two overlapping scans which provides a mechanism for correlating scans to normalize and/or reduce noise in scans. The fact that the multiple scans, covering a complete region, are acquired simultaneously improves the speed with which the complete region can be imaged or analyzed, thus reducing sensitivity to motion artifacts.

The deeper scans span regions of increasing magnitude, but in the same period of time, and therefore generate interferometric signals with different and increasing frequency content. This enables the multiple interferometric signals to be separated by processing in the electronic domain, which allows the simultaneous acquisition of scanned information from multiple depths.

Scans performed by using a piezo device are typically operated with a linear scan speed in the center region and slows to a stop at the extremes of the scan, often with a sine wave form characteristic. This may require only using a center region of the scan. The useful center region can be extended by electronic processing to compensate for or to reduce non-linear aspects.

Alternatively the piezo device may be operated with a true sine wave drive (without an extended linear region) and the resulting interferometric signals can be linearized by post processing. The preferred embodiment employs a piezo-electric device, however, other length modifying or modulating mechanisms, such as electro-mechanical or acousto-optic, can be used.

The depth separation 204 of the multiple scans is determined by the separation between the partially reflective element 110 and the modulating reflective element 111. The magnitude of the scans is determined by the magnitude of the single pass scan 205 or 208 and the number or order of passes, N. The scans that overlap and, therefore the region that can be completely scanned, is determined by both the depth separation 204 and the magnitude of the single pass piezo scan and the order of passes, N.

The magnitudes of the depth separation and single pass scan can be varied to suit particular applications. These magnitudes can be fixed for a particular design, or one or both magnitudes can be varied dynamically during operation. For example, a depth separation of 100 microns and a small single pass scan such as 2 microns enables simultaneous analyzing small segments over a range of 1 mm (with ten multi pass reflections or N of 10) within the target.

By varying the depth separation continuously from 100 microns to 50 microns (by, for example, controlling an offset of the piezo device) multiple offset sets of simultaneously acquired information can be accumulated thus effectively providing a complete scan of at least the deeper 0.5 mm of the 1 mm of the target being analyzed. An advantage of using a small single pass scan is that it can be accomplished at very high speed which makes each simultaneously acquired set of information less sensitive to motion artifacts.

Actively varying or modifying the depth or average spatial separation of different sets of segmented scans by, for example, controlling an offset of the piezo device 106 (of FIG. 1) enables interleaving sets of segmented scans that provide information about different regions of the target. In this manner composite continuous scans of a target can be generated from overlapping scan segments within a single set of segmented scans or from a sequence of sets of segmented scans with non-overlapping regions where different sets of segmented scans have different spatial separation between the partial reflective element 110 and the modulating reflective element 111 of FIG. 1.

Increasing the offset of the piezo device 106 will decrease the average separation 108 of the two reflective elements 110 and 111 (also referred to as the partially reflective element 110 and the modulating reflective element 111). This will decrease the average separation of the regions within the target that the reference signals relate to. More generally, modifying the average spatial separation 108 of the two reflective elements 110 and 111 modifies the average spatial relationship between different components of the reference radiation which in turn modifies the spatial relationship of the regions of the tissue that are effectively scanned by different components of the reference radiation.

The effect of introducing an increased offset of the piezo device 106 is illustrated by the set of scans 217 in FIG. 2. The offset reduces the spatial separation 216 of the set of segmented scans 217 and causes scanning in target regions that are not scanned by the set of scans 210 as indicated by the double arrow 218 pointing to an un-scanned region of the 210 set of scans and the same region in 217 set of scans which is scanned. In this manner a composite continuous scan can be generated from a sequence of segmented scans with non-overlapping regions where different sets of segmented scans have different average spatial separation determined by different piezo offsets.

An alternative to controlling an offset of the piezo device 106 to achieve different average spatial separation between the two reflective elements 110 and 111 (the partial reflective element 110 and the modulating reflective element 111) is illustrated in FIG. 1 where the partial reflective element is mounted on a translational device 112. In the preferred embodiment the translational device 112 is a second piezo device with a through hole for the reference radiation 105. For example, the translational device 112 can be used to control the average separation 108 at a relatively slow speed, while the piezo device 106 could modulate the modulating reflective element 111 at high speed. Various combinations of the piezo device 106 and the translational device 112 are possible.

Alternatively the translational device 112 can be other forms of piezo devices or electromechanical devices, such as voice coils. By such means substantial changes in the average spatial separation 108 between the two reflective elements 110 and 111. The average spatial separation 108 can be substantial in order to span large distances. For example in an ophthalmic application the average spatial separation 108 may be selected or dynamically controlled to have low order references signals correspond to surfaces at the front of the eye while higher order reference signals could correspond to surfaces or structures towards the back of the eye.

Accurate information about the separation or position of such surfaces can be determined by accurately monitoring the spatial separation 108 between the two reflective elements 110 and 111. This can be achieved by conventional position measurement techniques including, but not limited to, strain gauge; electrical capacitance; and optical techniques.

Figure 3:
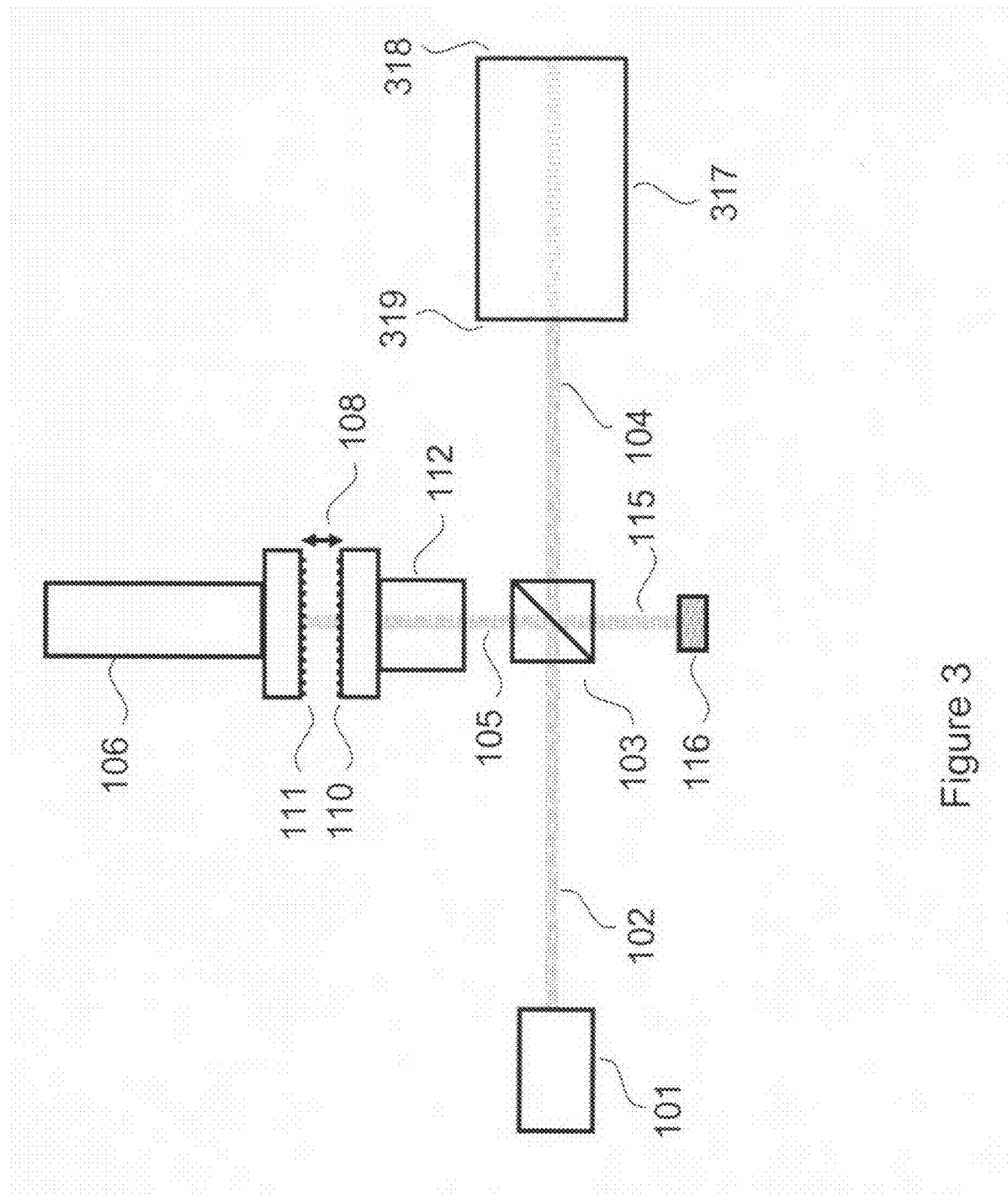
FIG. 3 is an illustration of an etalon based precision measurement module.

Alternatively accurate monitoring the spatial separation 108 between the reflective elements 110 and 111 can be achieved by use of one or more etalons as illustrated in FIG. 3, which in most respects is like FIG. 1, but where the target (109 of FIG. 1) is replaced with an etalon 317. The same numbers indicate corresponding components and are discussed previously.

By aligning the front surface 319 of the etalon with the modulating reflective element 111 and adjusting the separation 108 so that a high order reference signal scans the rear surface 318 of the etalon the magnitude of the separation 108 can be accurately determined from the known thickness and refractive index of the etalon, the order of the reference signal scanning the rear surface 318, the center wavelength of the SLD and the relative location of cycles of the first and higher order reference signals (which can be determined from the envelope of the interference signal).

This approach of using an etalon to monitor the separation 108 is particularly suitable situations where the nominal relative position of surfaces is known and any deviation from the nominal value is being monitored, or where one of a set of known etalons can be readily inserted.

Many variations of the etalon based monitoring are possible, for example, by having a partially reflective coating at the 319 surface and a highly reflective coating at surface 318 multiple reflections from the could be processed to extend the range of separation 108 that can be determined. Alternatively a composite or compound etalon involving more than two surfaces could be used. For example two etalons with slightly different thickness could be bonded together to form a compound etalon with three reflective surfaces.

The thickness difference provides a Vernier type mechanism to achieve very accurate position information when reflections from the three surface interact with multiple different order reference signals. The spatial separation 108 between the partial reflective element 110 and the modulating reflective element 111 (the reflective elements 110 and 111) can be monitored by processing composite interference signals generated by reflections from etalon surfaces.

Figure 4:
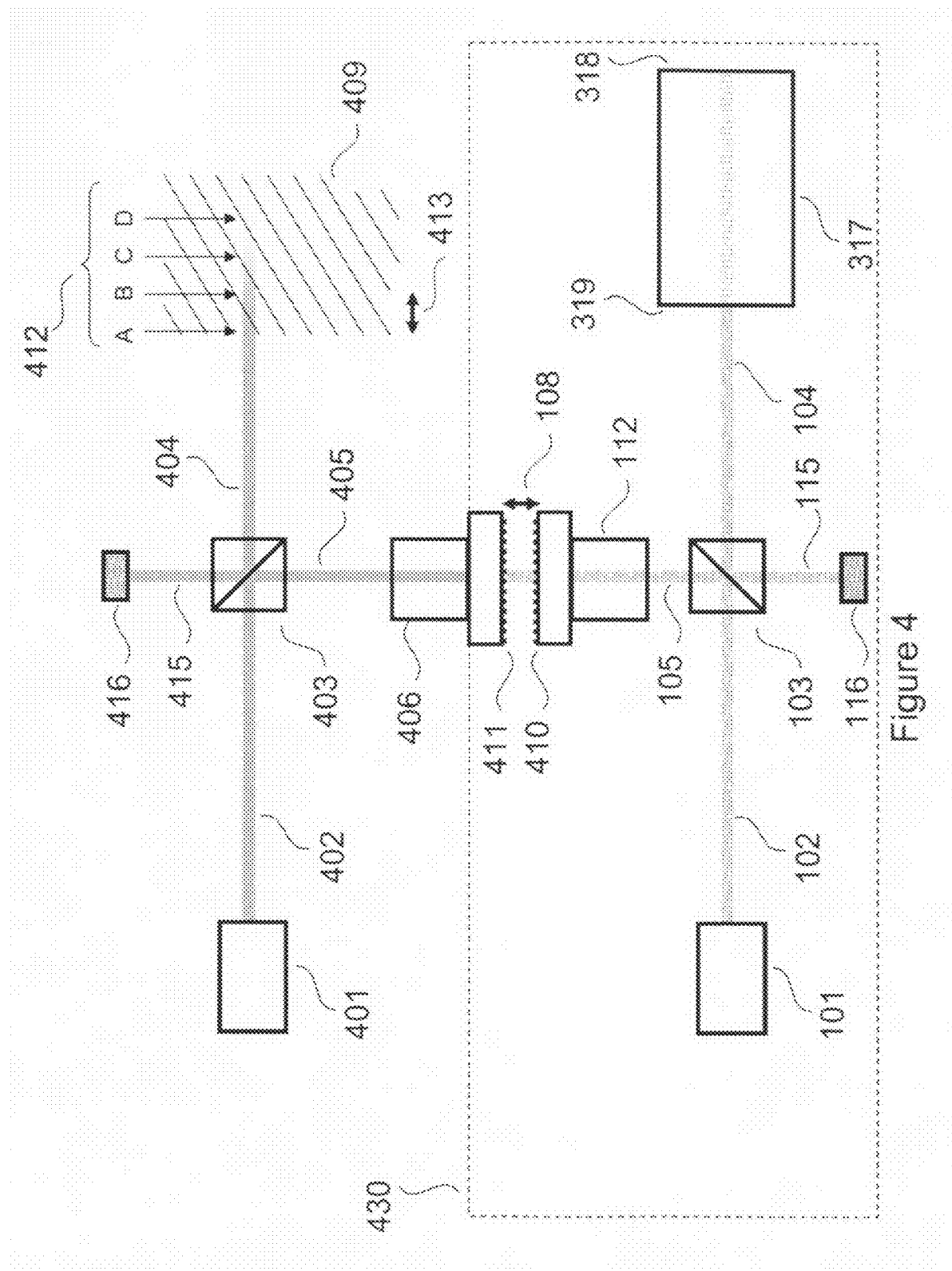
FIG. 4 is an illustration of a non-invasive imaging and analysis system including the etalon based precision measurement module according to the invention.

FIG. 4 illustrates how the etalon based separation monitoring module (illustrated in FIG. 3) may be integrated into a non-invasive imaging and analysis system. The etalon based separation monitoring module enclosed in dashed box 430 of FIG. 4 is substantially the same as that shown in FIG. 3, however, the reflective element 411 is partially reflective at a first wavelength range and highly reflective at a second wavelength range, while the reflective element 410 is highly reflective at the first wavelength range and partially reflective at the second wavelength range.

As illustrated in FIG. 4, this embodiment of the non-invasive imaging and analysis system includes an optical processing system that generates a probe beam and a reference beam from a broadband optical source 401 such as a super-luminescent diode or a mode-locked laser, operating at the first wavelength range, whose collimated output 402 consists of a broad band, discrete or continuous set of wavelengths. The first wave range is typically selected to optimize depth of penetration of the target under analysis.

The output beam 402, is passed through a beam splitter 403, to form a probe beam 404 and a reference beam 405 (which also becomes the composite reference beam on its return path). The probe beam 404 is applied to the target 409 of interest.

At least part of the radiation of the beam applied to the target is scattered back and captured form captured scattered probe radiation. The captured scattered probe radiation returns back to the beam splitter 403. The reference beam 405 (with the first wavelength range) is partially reflected by the reflective element 411. A portion of the reference beam is also transmitted through the reflective element 411 which is then reflected by the reflective element 410 to form a once modulated reference beam.

Modulation can be achieved by having the reflective element 410 mounted on a piezo device 112. Alternatively modulation can be achieved by having the reflective element 411 mounted on a (through-hole) piezo device 406. Various combinations of piezo devices or other translational or modulating devices can be used for elements 112 and 406 of FIG. 4.

As before, the composite reference beam, formed from multiple passes of the modulated reference beam, is combined with probe radiation back-scattered from the target 409 in the beam splitter 403. The resulting composite interference signals 415 are detected by the detector 416. As before different order reference signals relate to different depth locations, for example, depth locations indicated by the group 412 of arrows labeled A,B,C,D are separated by a distance 413 which is determined by the separation 108 modified by the refractive index of the target.

The separation 108 between the reflective elements 411 and 410 of is simultaneously monitored by the etalon based separation monitoring module enclosed in dashed box 430 of FIG. 4. This module operates at the second wavelength range which may be selected to be at a shorter center wavelength than the first wavelength range to facilitate more accurate separation measurement, or may be selected for reflective coating manufacturing reasons.

For example, a wavelength range centered on 400 nm would have a fundamental interference cycle of magnitude 200 nm, while the 20th. order reference signal would have an interference cycle of magnitude 10 nm. Involving relative phase information and higher order or combinations of high order reference signals enables sub-nanometer accuracy in monitoring relative positions of structures or surfaces.

Figure 5:
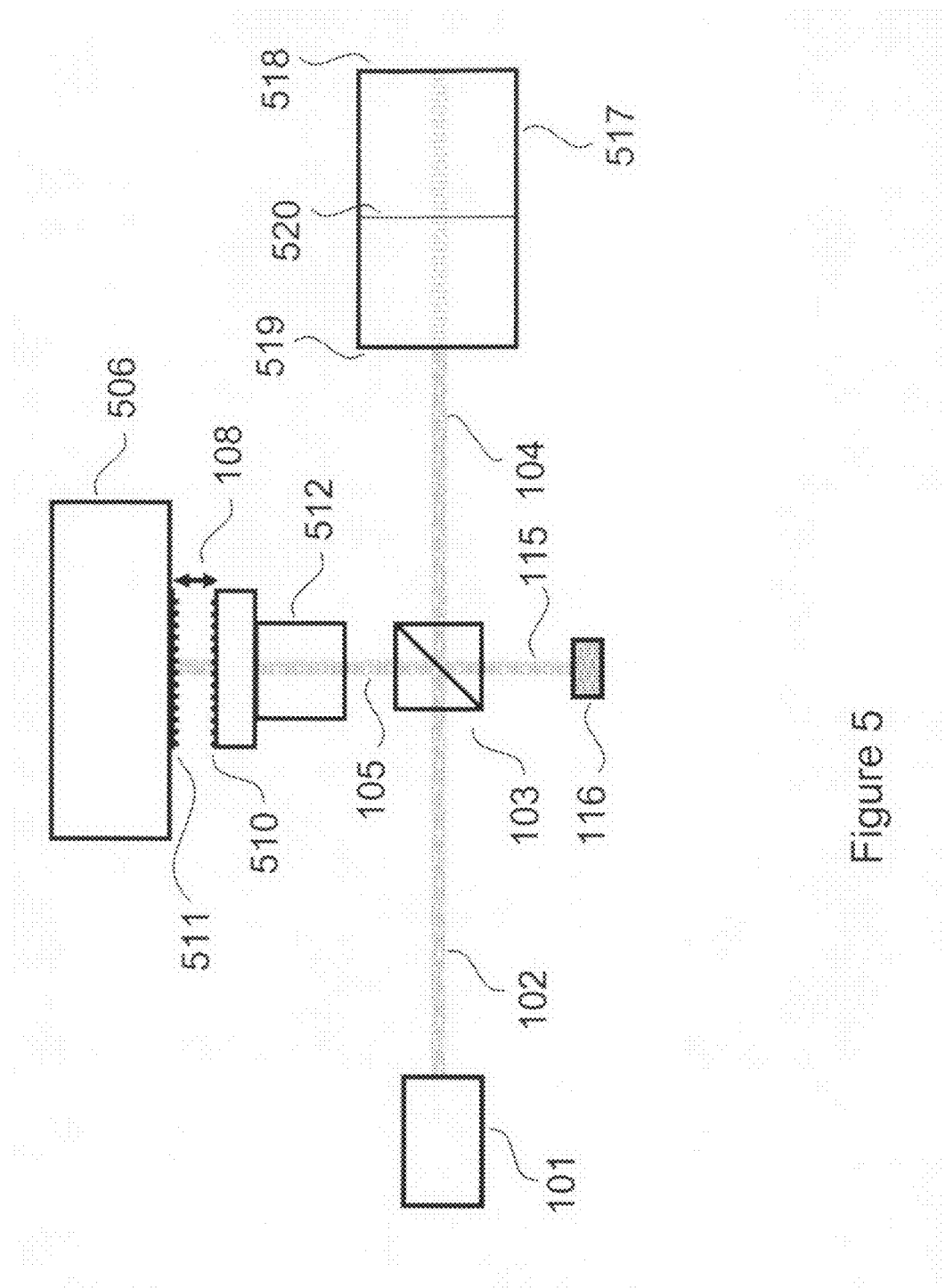
FIG. 5 illustrates a precision position measuring system using at least one etalon.

FIG. 5 illustrates a precision position measuring system using at least one etalon. The system is similar to that described in FIG. 3 in many respects. The same numbers indicate corresponding components and are discussed previously. In this embodiment the reflective element 511 is coupled to or otherwise in contact with an object of interest 506 the position of which is to be monitored. A position change of the reflective 511 causes changes in the spatial separation 108 which causes changes in the multiple reflections between the reflective elements 511 and 510 where the reflective element 510 is a partially reflective element.

The reflective element 510 is mounted on a length modifying device 512, which in the embodiment illustrated in FIG. 5, is a piezo device (with a through hole) operable at high speed to make the reflective element 510 a modulating reflective element. In this embodiment the reflective element 511 typically modifies the spatial separation between the reflective elements 511 and 510 at a relatively slow speed.

Reflections from the compound etalon 517 when combined with the reflections from the reflective elements 511 and 510 generate composite interferometric signals which when analyzed provide highly precise position information about the object 506. The compound etalon 517 illustrated here shows three reflective surfaces 518, 519, 520, a first second and third reflective surface respectively. It can be appreciated that an etalon with more reflective surfaces may be used or more than one etalon provided the system has appropriate processing capabilities. The resulting precise position information may, for example, be used in a feed-back system to precisely control the position of the object of interest 506.

The object 506 whose position can be accurately monitored by monitoring the separation 108 between the two reflective elements 511 and 510 could, for example be a component in an optical system. The object 506 could also be a deformable adaptive optic. Multiple precision position measuring systems could be used to accurately monitor the positions of multiple locations of a deformable adaptive optic. Alternatively a single precision position measuring systems with multiple output beams formed by an array of collimating lenses could be used to accurately monitor the positions of multiple locations of a deformable adaptive optic.

The preferred embodiments that are illustrated are free space configurations. Equivalent configurations could be implemented in optical fiber or in combinations of free space and optical fiber. In such designs or configurations beam splitters could be replaced by fiber couplers. Mirrors could be replaced by fiber reflective elements, such as fiber loops or Bragg gratings.

It can also be appreciated that there are many approaches to imposing different frequency content on different components of reference radiation to form composite reference radiation including those cited in the references. For purposes of this invention, any method, apparatus or system that modifies reference radiation such that when combined with a portion of probe radiation or scattered probe radiation, an composite interference signal is generated that has interference components that correspond to different components of the reference radiation and these different interference components have different frequency content.

Many variations of embodiments are possible. Position tracking by the separation monitoring module can include counting cycles of one order as they move with respect to a lower order. Relative phase information can be used to achieve greater precision. Different higher orders can be used at different length ranges, with interpolation in between. Compound etalons can be used to provide more accurately positioned surfaces. Narrow band SLD can be used for more continuous range while still maintaining the ability to a distinguish peak cycle. Optional focusing lenses may be used to focus radiation into targets or onto reflective elements.

The preferred embodiment uses an SLD as the optical source, however other broad-band optical sources such as mode-locked lasers could be used. In the case of a mode-locked laser as the source the reference path length and the probe path length have to be either equal or different by an integral number the length corresponding to the repetition period of the repetitive mode-locked pulse train. This is possible because a mode-locked pulse train has a repetitive nature.

This enables the opportunity to have a compact micro-bench optical system but a long probe length which facilitates fiber delivery of the probe signal, which in turn facilitates catheter based internal imaging and analysis. Non-optical sources of broadband radiation may be used including, but not limited to, acoustic radiation including ultra-sound radiation, micro-wave radiation, X-radiation, Also, while the preferred embodiment describes imaging and analyzing biological entities, such as structures and surfaces within the eye, the invention is generally applicable to non-invasive imaging and analysis of characteristics of interest in targets under analysis. For example the invention could be used for surface position tracking for adaptive optics.

Many of the features of this invention have functional equivalents that are intended to be included in the invention as taught. For example, the optical source could include multiple SLDs with either over-lapping or non-overlapping wavelength ranges, or, in the case of a mode-locked laser source could be an optically pumped mode-locked laser, or could be a solid state laser, such as a Cr:LiSAF laser optically pumped by a diode laser. The optical source could be passively mode locked by a Kerr lens or by a semiconductor saturable absorber mirror. Gain switched optical sources, with optical feedback to lock modes may also be used.

The optical source could include band-width broadening mechanisms, including, but not limited to, continuum generation. Such continuum generation based techniques include using wave-guide based micro-rings containing highly non-linear material or photonic crystals and non-linear fiber, such as photonic crystal or holy fiber. For purposes of this invention, mode-locked lasers will include gain switched optical sources band-width broadening mechanisms.

It can be appreciated that the system and method taught herein may be performed by either a free standing device with internal processing. Alternatively a free standing device may be coupled with a remote processing system.

Other examples will be apparent to persons skilled in the art. The scope of this invention should be determined with reference to the specification, the drawings, the appended claims, along with the full scope of equivalents as applied thereto.

What is claimed is:

1. A method of scanning a target, said method comprising:
    generating probe radiation;
    generating reference radiation;
    imposing different frequency content on different components of said reference radiation to form composite reference radiation;
    modifying the average spatial relationship between said different components of said reference radiation by modifying the average spatial separation between a first and a second reflective elements in the path of the reference radiation, where said first reflective element is a partially reflective element and said second reflective element is a highly reflective element, whereby said modification of said average separation modifies the regions of the target that are scanned;

applying said probe radiation to said target;

capturing at least part of said probe radiation scattered from within said target to form captured scattered probe radiation;

combining said captured scattered probe radiation and said composite reference radiation to form a composite interferometric signal; and processing said composite interferometric signal to achieve a scan of said target, where said scan is composed of different sets of scan segments obtained at different average spatial separations between said first and said second reflective elements.

2. The method of claim 1, wherein the step of modifying the average spatial relationship between said different components of said reference radiation further includes monitoring the magnitude of the average spatial relationship between said different components of said reference radiation by monitoring the average spatial separation between said first and second reflective elements using conventional position measuring techniques.

3. The method of claim 1, wherein modifying the average spatial relationship between said different components of said reference radiation further includes monitoring the magnitude of the average spatial relationship between said different components of said reference radiation by monitoring the average spatial separation between said two reflective elements by processing composite interference signals wherein said composite interference signals include reflections from etalon surfaces, wherein said etalon surfaces are in the probe path of a second optical analysis system using an optical source operating at a second wavelength range and using said two reflective elements.

4. The method of claim 1, wherein processing said composite interferometric signal to achieve a scan of said target includes achieving a composite continuous scan generated from a sequence of segmented scans with non-overlapping regions wherein different sets of segmented scans have different average spatial separation.

5. The method of claim 1, wherein generating probe radiation includes generating a first and second probe radiation, wherein said first probe radiation is at a first wavelength range and wherein said second radiation is at a second wavelength range;

generating a first reference radiation at said first wavelength range;

generating a second reference radiation at said wavelength range;

imposing different frequency content on different components of said first and second reference radiation to form a first and second composite reference radiation;

modifying the average spatial relationship between said different components of said first reference radiation;

applying said second probe radiation to said etalon;

capturing at least part of said second probe radiation reflected from said etalon to form captured reflected probe radiation;

combining said captured reflected probe radiation and said second composite reference radiation to form a second composite interferometric signal; and processing said second composite interferometric signal to monitor the average spatial relationship between said different components of said second reference radiation;

applying said first probe radiation to said target;

capturing at least part of said first probe radiation scattered from within said target to form captured scattered probe radiation;

combining said captured scattered probe radiation and said first composite reference radiation to form a first composite interferometric signal; and processing said first composite interferometric signal to achieve a scan of said target.

6. The method of claim 5, wherein at least one reflective element is partially reflective at a first wavelength range and highly reflective at a second wavelength range.

7. The method of claim 5, wherein at least one reflective element is partially reflective at said second wavelength range and highly reflective at said first wavelength range.

8. A system for scanning a target, said system comprising:
means for generating probe radiation,
means for generating reference radiation,
means for imposing different frequency content on different components of said reference radiation to form composite reference radiation,
means for modifying said different components of said reference radiation by modifying the average spatial separation between a first and a second reflective elements in the path of the reference radiation, where said first reflective element is a partially reflective element and said second reflective element is a highly reflective element, whereby said modification of said average separation modifies the regions of the target that are scanned,
means for applying said probe radiation to said target,
means for capturing at least a portion of said probe radiation scattered from within said target to for captured scattered probe radiation,
means for combining said captured scattered probe radiation and said composite reference radiation to form a composite interferometric signal; and
means for processing said composite interferometric signal to achieve a scan of said target, where said scan is composed of different sets of scan segments obtained at different average spatial separations between said first and said second reflective elements.

9. The system of claim 8 wherein said means for modifying said different components of said reference radiation includes a means to modify the average spatial relation between two reflective elements, where said reflective elements are in the path of said reference radiation.

10. The system of claim 9 further including a means to monitor said average spatial relationship between said different components of said reference radiation.

11. The system of claim 10 wherein said means to monitor said average spatial relationship between said different components of said reference radiation further includes a means to monitor the average spatial relationship between said two reflective elements.

12. The system of claim 11 wherein said means to monitor said average spatial relationship between said two reflective elements includes conventional position measuring techniques.

13. The system of claim 11 wherein said means to monitor said average spatial relationship between said two reflective elements includes a means to process composite interference signals, where said composite interference signals result from reflections from at least one etalon.

* * * * *